United States Patent [19]

Plapp

[11] 4,358,118
[45] Nov. 9, 1982

[54] ELECTRONIC GAME USING A PLAYER'S PHYSIOLOGICAL RESPONSES

[76] Inventor: Gary R. Plapp, P.O. Box 572, Redwood Estates, Calif. 95044

[21] Appl. No.: 128,194

[22] Filed: Mar. 7, 1980

[51] Int. Cl.$^3$ ............................................. A63F 9/00
[52] U.S. Cl. .............................. 273/85 G; 273/1 GC
[58] Field of Search ................. 273/1 GC, 1 E, 85 G, 273/DIG. 28; 128/905, 731–734; 272/86 R, 86 B, 73; 358/93

[56] References Cited

U.S. PATENT DOCUMENTS

| | | | |
|---|---|---|---|
| 3,419,732 | 12/1968 | Lane | 272/57 |
| 3,855,998 | 12/1974 | Hidalgo-Briceno | 273/1 E X |
| 3,893,450 | 7/1975 | Ertl | 273/DIG. 28 |
| 3,991,304 | 11/1976 | Hillsman | 128/720 |
| 4,149,716 | 4/1979 | Scudder | 273/85 G |
| 4,171,696 | 10/1979 | John | 128/731 |

OTHER PUBLICATIONS

Saladin, J. J. and Bohman, C. E.; "Anaglyphic T.V. 'Ping Pong' Antisuppression Trainer"; *Journal of American Optom. Association;* Jul. 1977; pp. 929–932.
*Radio–Electronics;* "Mind Power: Alpha" (Part I); Jul. 1976; pp. 36–39, 91.
*Radio–Electronics;* "Mind Power: Alpha" (Part IV); Sep. 1976; pp. 49–51, 56.
*Radio–Electronics;* "IC Application of the Month"; Jan. 1977; pp. 61–65.

Primary Examiner—Vance Y. Hum
Attorney, Agent, or Firm—Flehr, Hohbach, Test, Albritton & Herbert

[57] ABSTRACT

An electronic game for one or more players senses physiological responses of each player's body indicative of the level of calmness of the player. These responses are compared to those of the other player (or to a reference level established by the machine) in order to score points whenever the difference between calmness levels exceeds a predetermined degree. Points are counted in a visual display associated selectively with whichever player has, according to the game, either the lower or higher level of calmness.

4 Claims, 4 Drawing Figures

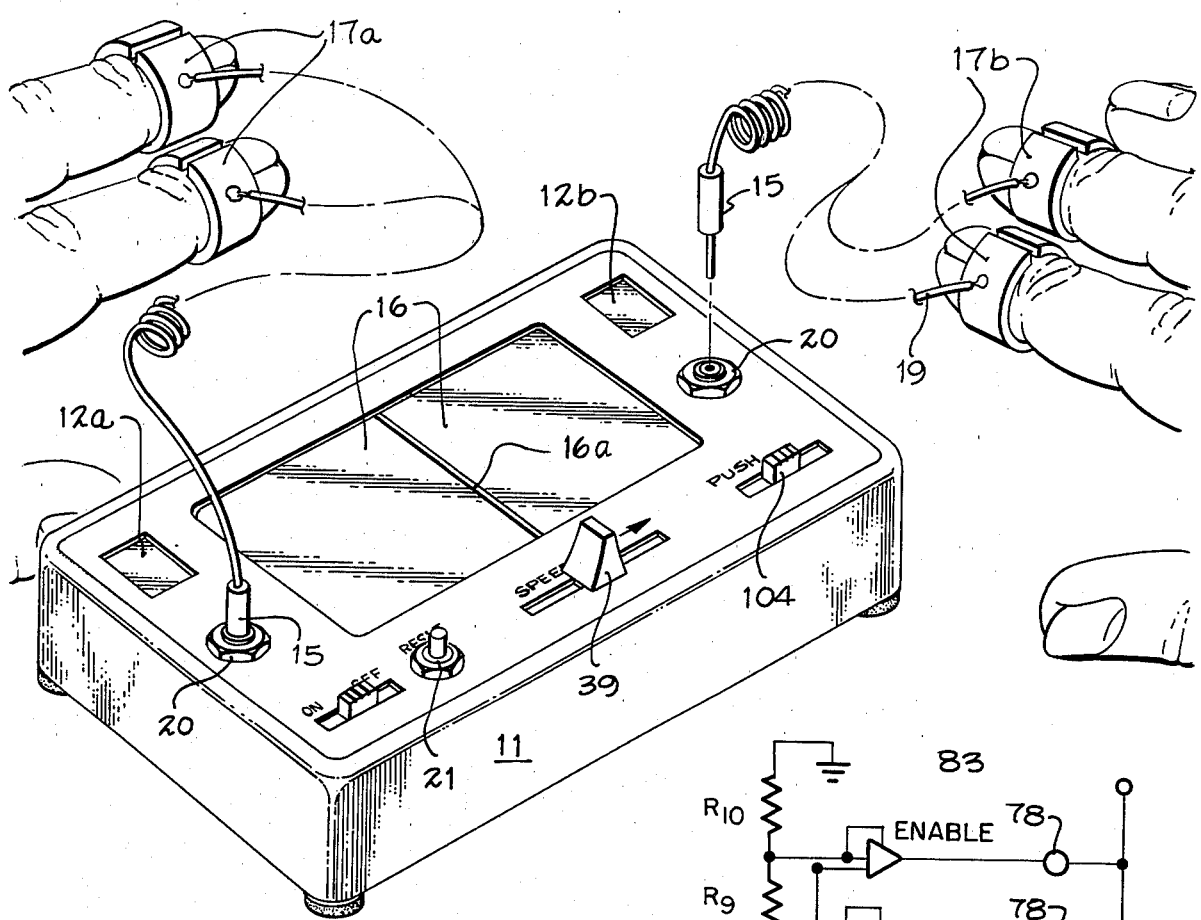
FIG_1
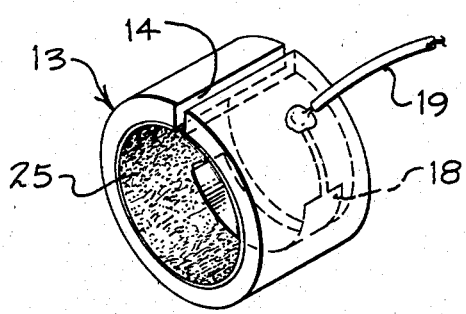
FIG_2
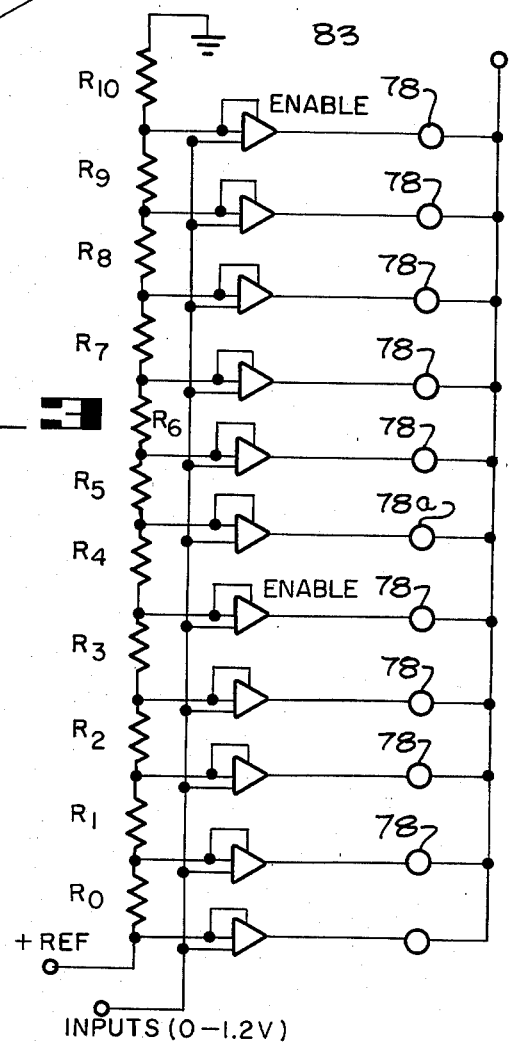
FIG_3

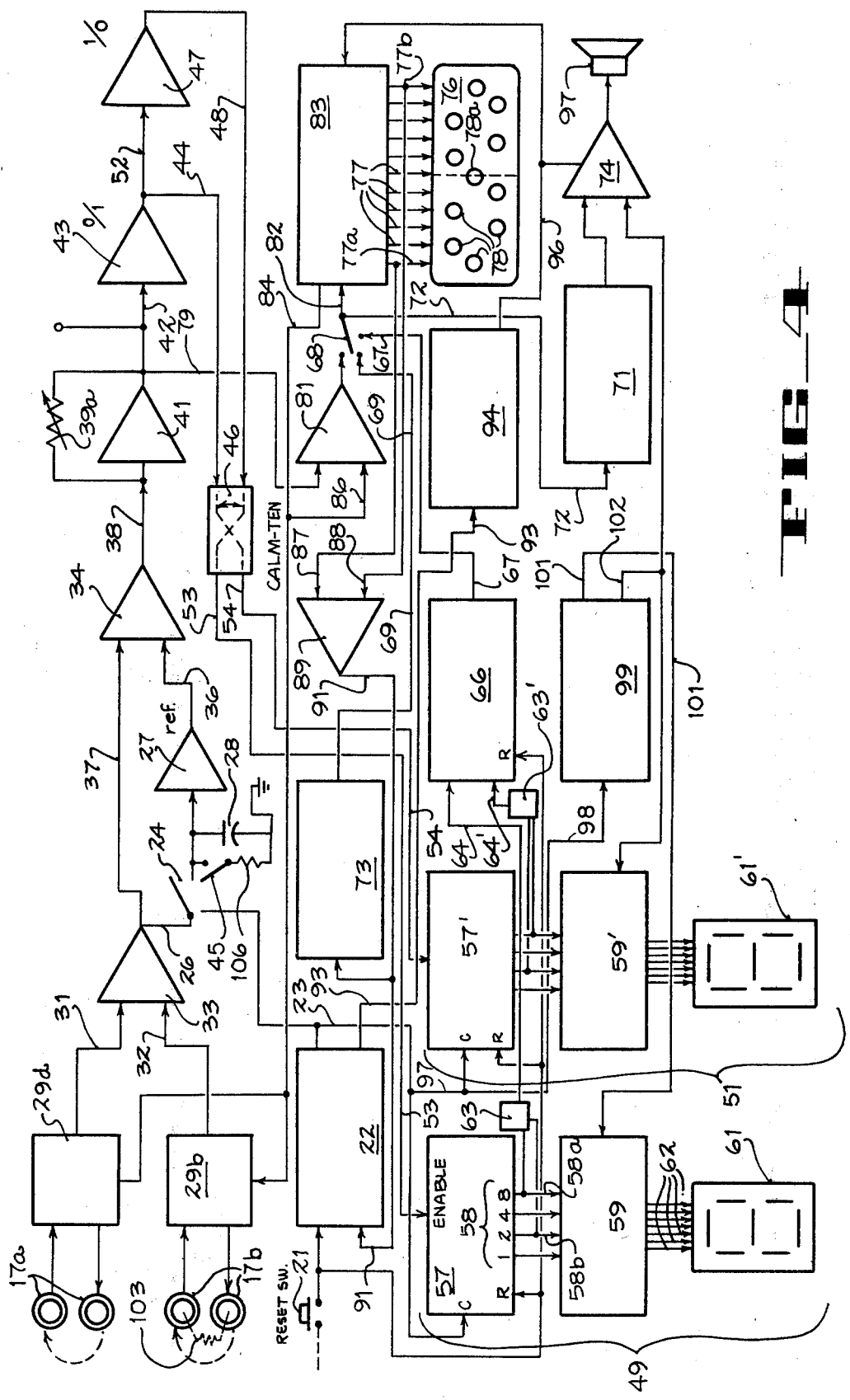

ELECTRONIC GAME USING A PLAYER'S PHYSIOLOGICAL RESPONSES

This invention pertains to an electronic game and more particularly to an electronic game activated in response to a player's physiological responses.

Heretofore most electronic games have been operated or actuated by manipulations of controls by the player. As disclosed herein an electronic game is provided in which the physiological responses of a player are sensed to provide inputs to the system for purposes of scoring points. For example, in one embodiment points are scored by the player who is the most calm. According to another embodiment points are scored by the player who is the most tense.

In another embodiment points are scored by a player operating against the machine itself whereby the level of calm or "tense" of the machine is provided as a standard or which varies.

Accordingly, it is an object of the present invention to provide an improved electronic game construction.

It is a further object of the present invention to provide an improved electronic game construction responsive to physiological functions of the body.

It is yet another object of the present invention to provide an improved electronic game construction of the type wherein a pair of players can play against each other or a player can play against the machine using physiological responses of the body as inputs.

The foregoing and other objects of the invention will be more clearly understood when considered in conjunction with the following detailed description and drawings.

FIG. 1 shows a diagrammatic perspective view of a game according to the invention;

FIG. 2 shows a diagrammatic perspective view of an electrode according to the invention;

FIG. 3 shows a schemmatic view of an LED display according to the invention; and FIG. 4 shows a block diagram arrangement of the system according to the invention.

The electronic game 10 includes a case 11 containing the electronics of FIG. 4. The score for each player appears in the related scoring window 12a, 12b for player positions #1 and #2 respectively. A pair of electrodes 13 serve to sense the galvanic skin response of the tips of a player's fingers. Electrodes 13 are of semi-stiff material and formed with a split 14 to permit it to fit a wide range of finger sizes. Within the ring-like portion, a lining of conductive foam material 25 is disposed to provide a uniform contact to the finger. An electrode plate 18 is glued to the inner surface of the ring-like portion and coupled to the lead 19 which carries a plug 15 for entry into an associated jack 20.

As shown in FIG. 4 the system operates by closing a reset switch 21 so as to activate a one-shot timer circuit 22 to provide a prolonged output pulse of the order of 2½ seconds on lead 23.

The presence of the pulse on lead 23 serves to operate the sample and hold switch 24 to supply the value of signals on lead 26 to a sample and hold circuit 27. While at the same time loading the capacitor 28.

Prior to operating the reset switch 21 two players, for example dispose their associated finger sensors 17a, 17b onto their fingers as noted above. Each pair of finger sensors is coupled in circuit serially with an associated constant current generator 29a, 29b providing a DC current on the order of 1.5 micro amperes.

In view of the fact that the skin resistance of a person's fingers can vary from various physiological conditions as noted above, as the resistance of a person's fingers increases the voltage tends to increase. Inasmuch as the current in each of generators 29 is maintained constant, the voltage must be adjusted upwardly in order to maintain a constant relationship.

In short, as the finger resistance increase the voltage output from the associated current generator 29 increases.

Accordingly, after the reset switch 21 is closed and with the players wearing their respective finger sensors 17 associated voltages are provided as inputs 31, 32 with differential amplifier 33 to provide an initial output reading on lead 26.

Accordingly, as the result of the prolonged output pulse applied to lead 23 and the sample and hold switch 24 is closed to supply this initial relationship via lead 26 to sample and hold circuit 27. Accordingly, a reference voltage is provided to the differential amplifier 34 via lead 36 while a substantially similar relationship will be supplied to the differential amplifier 34 via lead 37 at the outset of the game. Accordingly, at that point the position of the "ball" or other indicator shown on the screen 16 will appear beneath the midline 16a as the result of the voltage appearing on line 38. The speed control knob 39 goes between advanced and retracted positions to increase or decrease the effect of the sensitivity amplifier 41. Thus, the control knob 39 operates the variable resistance 39a as shown in FIG. 4.

Assuming that the operation of the system shown in FIG. 4 is to be described with regard to a contest between two particular players who are respectively attempting to become calmer than the other whereby the calmest player will score the most points and thereby win the game, in order to score a point it is necessary to cause the voltage at line 42 to move one volt from zero. Accordingly, there is a voltage swing on line 42 between plus and minus one volt. Accordingly, a Schmitt trigger 43 provides a digital zero or digital one depending upon the state of the trigger 43 which is operated by the attainment of plus or minus one volt on line 42.

Thus the output from trigger 43 on lead 44 is fed to the reverse score switch 46 via lead 44 and also via inverter 47 and lead 48. The output of switch 46 leads to one or the other of the two scoring units 49, 51 for enabling same in response to a logical one appearing on lead 44.

As shown, with the reverse score switch 46 in the position noted a logical one on lead 44 will serve to enable the scoring unit 51 while the scoring unit 49 is diabled due to the presence of a logical zero on lead 48. When a logical zero appears on lead 52 then the reverse is true. Display driver 83 is of the bar or dot graph style and provides outputs in linear ten percent increments with a zero point at the center thereof. Accordingly, the signal conditioner 81 serves to receive a reference signal via lead 84 and 86 to be compared to the input via lead 79. Inasmuch as the range of display driver 83 is zero to plus 1.2 volts and the range of the signals on lead 62 is plus or minus one volt the signal conditioner 81 serves to correlate the two so as to convert the input signals to signals for application to the display, commencing with a zero position at element 78a which actually represents 0.6 volts, i.e. half 1.2 volts.

At such time as the end LED elements 78 are activated by signals on lines 77a or 77b a signal is fed via lead 87 or 88 to be fed into a score comparator 89.

The output from comparator 89 is redirected to the one-shot timer unit 22 which has the effect of resetting the system to commence play for an additional point. In addition the end of game display generator 73 also senses the foregoing signal via lead 91 to cause same to advance.

The signal supplied to the one-shot timer unit 22 serves to genrate an output via lead 93 to be supplied to a modulator unit serving to modulate the playing tone associated with the machine as well as to modulate the display to cause the dots to be lighted back and forth in a cyclic manner. Accordingly, the output from the play tone and display modulator unit 94 appears on line 96 for activating the tone signal conditioner driver 74. The signal on lead 96 further serves as a blanking signal with respect to the moving dot display driver 83 representative of the end of the routine for a given point.

Finally, while not mentioned above, when the one-shot timer unit 22 provides an output signal on lead 23 that signal also travels along a path defined by the leads 97 and 98 to enable the score and dual tone generator and LED display/digit modulator unit 99. Unit 99, accordingly, serves via lead 101 to enable the decoder driver unit 59 and via lead 102 to enable the decoder and driver unit 59'.

While the foregoing arrangement has been described with respect to a condition in which the reverse score switch 46 is arranged to score points for the player who demonstrates the greatest degree of being calm, by reversing the switch it is possible to score points in the same manner for the player who becomes the most tense.

In addition to the above, a thermistor probe can be used with electrode 13 or otherwise employed by a player, since thermistor variations in resistance are known to occur with respect to temperature.

The output from the one-shot timer unit 22 appearing on lead 93 serves to inhibit play tone and display modulator 94 so as to turn it off. Accordingly, the output signal therefrom on lead 96 serves as a blanking pulse to the moving dot display driver 83 as well as to inhibit the tone signal conditioner driver 74.

The two scoring units 49, 51 are each constructed in the same manner and a description of one is believed to constitute a sufficient description of both. Accordingly, a binary coded decimal counter 57 when enabled by an appropriate logical "1" appearing at its input 53 (or 54 for unit 51) serves to trigger the count in counter 57 upwardly one number at a time, the output therefrom appearing on lines 58. Lines 58 each represent a binary stage starting with the leftmost line representing the numeral one and the right hand line 58a representing the numeral eight.

Signals appearing on these four lines 58 represent an input to the decoder and driver unit 59 coupled to the seven segment display 61. Thus, decoder/driver unit 59 serves to convert the binary coded decimal inputs to outputs for operating the seven segment display 61. These outputs, of course, appear on lines 62.

The display 61 serves to count from zero to nine. A point scored after numeral 9 has been entered completes the game. Accordingly, upon reaching a count of ten (as disclosed herein) an end of game signal is generated via the AND gates 63 or 63' in response to the conjoint receipt of signals from lines 58a and 58b, or 58a' and 58b'. Accordingly, an output signal from AND gate 63 will appear on line 64 for activating the end of game switch driver 66.

Thus, upon sensing the end of the game, driver 66 provides an output signal on line 67 for operating the electronic switch 68 to couple lead 69 to the input 82 of moving dot display driver 83 and the voltage controlled oscillator-play tone unit 71 via lead 72. Lead 69 is coupled to an end of game display generator 73 such as a flip-flop acting as a sawtooth generator or the like.

Beneath the transparent screen 16 lies a plurality of lights which can be lighted in sequence to progressively advance toward one end or the other of an LED display unit 76. In general as one of the players becomes calmer than the other player the lighted dots will progress toward that end of the screen 16 associated with the calmer player. Accordingly, as shown in FIG. 4 the LED display 76 is supplied from a plurality of eleven inputs 77 coupled to a moving dot display driver such as shown in FIG. 3. Display 76 includes a number of LED elements 78 wherein element 78a is disposed in the middle of screen 16. Accordingly, as the voltage moves in one direction or the other the lights become lighted to the exclusion of the others.

During play signals taken from line 42 via lead 79 can vary between plus and minus one volt.

These signals are delivered to a signal conditioning circuit 81 which supplies an input via lead 82 to a moving dot display driver 83.

While the foregoing arrangement of the system has been described with respect to a pair of players playing against each other, in the event that a single player desires to utilize the game by himself, the system as disclosed in FIG. 4 is arranged whereby by suitable known means and with the prong 15 of the electrode associated with player No. 2 removed from its associated jack, a resistance 103 is disposed across the leads to the constant current generator 29b. Accordingly, a steady value of resistance will be provided by the player No. 2 position whereby the player can compete against the machine.

In addition to the above and according to another embodiment when the mode switch 104 is moved to the "push" mode a switch 45 places a relatively large resistance 106 across capacitor 28 so as to bleed the charge from 28 and thereby provide an ever changing reference value to be supplied to differential amplifier 34.

I claim:

1. An electronic game of a type in which players compete comprising a plurality of constant current input means adapted to be associated with a respective one of a plurality of players for detecting the of the player's skin indicative of the level of calm of the player, means for sensing the difference in said level between the players, means for indicating a predetermined degree of difference in said level of calm between the players, means for detecting whenever said difference exceeds said predetermined degree, means for keeping count of each time said difference exceeds said predetermined degree, a plurality of said scoring displays adapted to be respectively associated with said plurality of players, and means for scoring each said count in that one of scoring displays associated with the calmer player.

2. An electronic game of a type in which players compete comprising a plurality of constant current input means adapted to be respectively associated with a plurality of players for applying said current thereto, said input means serving to detect the electrical resistance of the player's skin, said resistance changing in response to variations in the degree of calm of the player, display means responsive to said inputs for indicating the difference between the degree of calm of one of the players and that of another player, means for indicating a predetermined degree of difference in said level of calm between the players, means for detecting whenever said difference exceeds said predetermined degree of difference, means responsive to the last named means for counting each said detection and for displaying the score thereof selectively associated with the calmer or less calm player.

3. An electronic game of a type in which players compete comprising a plurality of input means adapted to be respectively associated with a plurality of players for sensing electrical resistance at the skin of an associated player's body indicative of the level of the calm of the player, means for sensing changes in the difference between the calm level of one of the players and that of another player, display means responsive to the last named means for indicating progressive changes in said difference, means for indicating a predetermined degree of difference in said level of calm between the players, means for detecting whenever said difference exceeds said predetermined degree of difference, means responsive to the last named means for counting each said detection, and means for displaying the score thereof associated selectively with whichever player has, according to the game, either the lower or higher level of calm.

4. An electronic game of a type in which a player competes comprising input means for sensing electrical skin resistance of a player's body indicative of the degree of calmness of the player, means for indicating a reference level of calmness, display means responsive to said input means for indicating a difference between the degree of calmness of the player and that of said reference level, means for indicating a predetermined degree of difference in the calmness between the player and said reference level, means for detecting whenever said difference exceeds said predetermined degree of difference, means responsive to the last named means for counting each said detection, and means for displaying the score thereof associated selectively with the player or the reference level whichever represents, according to the game, either the lesser or greater calmness.

* * * * *